(12) United States Patent
Löffert et al.

(10) Patent No.: US 11,597,963 B2
(45) Date of Patent: Mar. 7, 2023

(54) MICROBIAL SELECTION SYSTEM

(71) Applicant: BIOMILLENIA SAS, Romainville (FR)

(72) Inventors: Dirk Löffert, Haan (DE); Eric Shiue, Paris (FR); Aleksander Dajkovic, Paris (FR); Guansheng Du, Ivry sur Seine (FR)

(73) Assignee: BIOMILLENIA SAS, Paris (FR)

( * ) Notice: Subject to any disclaimer, the term of this patent is extended or adjusted under 35 U.S.C. 154(b) by 0 days.

(21) Appl. No.: 16/762,733

(22) PCT Filed: Nov. 9, 2018

(86) PCT No.: PCT/EP2018/080827
§ 371 (c)(1),
(2) Date: May 8, 2020

(87) PCT Pub. No.: WO2019/092213
PCT Pub. Date: May 16, 2019

(65) Prior Publication Data
US 2020/0263225 A1 Aug. 20, 2020

(30) Foreign Application Priority Data

Nov. 9, 2017 (EP) .................................... 17200922

(51) Int. Cl.
*C12Q 1/00* (2006.01)
*C12Q 1/18* (2006.01)
*C12Q 1/04* (2006.01)

(52) U.S. Cl.
CPC ....... *C12Q 1/18* (2013.01); *C12Q 1/04* (2013.01)

(58) Field of Classification Search
CPC ...................................................... C12Q 1/00
See application file for complete search history.

(56) References Cited

U.S. PATENT DOCUMENTS 3,607,648 A * 9/1971 Yoneda .................. C12P 19/02
435/105

OTHER PUBLICATIONS

Kaminski etal (Lab Chip vol. 16, pp. 2168-2187) (Year: 2016).*
Office Action mailed by the European Patent Office for European Application No. 18 810 894.8-118 (Applicant—Biomillenia SAS) (8 Pages).
Najah, et al. "Droplet-Based Microfluidics Platform for Ultra-High-Throughput Bioprospecting of Cellulolytic Microorganisms" Chemistry & Biology, vol. 21, No. 12, Dec. 2014, pp. 1722-1732.

* cited by examiner

*Primary Examiner* — Albert M Navarro
(74) *Attorney, Agent, or Firm* — Ballard Spahr LLP

(57) ABSTRACT

The invention relates to a method for the identification of a first microorganism potentially secreting an effector compound, said first microorganism thereby having either i. an inhibitory effect on the cell division activity of a second microorganism or ii. an enhancing effect on the cell division activity of a second microorganism, the method comprising: a. providing a cell from a first microorganism which potentially produces an effector compound of interest and a cell from a second detector microorganism; b. introducing both cells into a microdroplet for incubation; c. introducing the microdroplet into a microfluidic system; d. analyzing in said microfluidic system the cell of the second microorganism for the exhibition of an enhanced growth effect or the exhibition of an inhibited growth effect stemming from said effector compound. The invention also relates to a microorganism or effector compound identified by the method according to the invention.

6 Claims, 10 Drawing Sheets

Specification includes a Sequence Listing.

```
                        SEQUENCE LISTING

<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: Forward primer

<400> SEQUENCE: 1
tacacgtact tagtcgctga agctcttcta tggtgagcaa gggcgaggag                50

<210> SEQ ID NO 2
<211> LENGTH: 53
<212> TYPE: DNA
<213> ORGANISM: Artificial Sequence
<220> FEATURE:
<223> OTHER INFORMATION: Reverse primer

<400> SEQUENCE: 2
taggtacgaa ctcgattgac ggctcttcta ccctaaagct tgtacagctc gtc           53
```

MICROBIAL SELECTION SYSTEM

CROSS REFERENCE TO RELATED APPLICATIONS

This application claims the benefit of priority under 35 U.S.C. § 371 of International Application No. PCT/EP2018/080827, filed on Nov. 9, 2018, which claims the benefit of European Application No. 17200922.7, filed on Nov. 9, 2017. The content of these earlier filed applications are hereby incorporated by reference herein in their entirety.

REFERENCE TO SEQUENCE LISTING

The Sequence Listing submitted May 8, 2020 as a text file named "37578_0074_U1_Sequence_Listing.txt," created on May 7, 2020, and having a size of 546 bytes is hereby incorporated by reference pursuant to 37 C.F.R. § 1.52(e)(5).

FIELD OF THE INVENTION

The present application is in the field of cell culture analysis, more precisely in the field of cell culture analysis on single cell level. The application is also in the field of microfluidics, in particular in the field of microfluidic analysis and devices.

BACKGROUND

The production of biological compounds such as sugars, amino acids, antibiotics, carbon sources or nitrogen sources and other chemical building blocks and natural products today is often efficiently performed in microorganisms. With the tools of genetic engineering it is possible to optimize microorganisms for an increased production of compounds. But also microorganisms that occur in the environment or live associated with organisms such as plants, animals or humans produce commercially interesting natural substances or are themselves of commercial interest, e.g. as biofertilizers, biopesticides or probiotics.

These optimized microorganisms are generated using different mutagenic/combinatorial strategies capable to generate large libraries of genetically modified organisms. However, the drawback or bottleneck of all strategies are the screening methods used to analyze individual library members.

The relevant screening methods are dependent on the molecules to be produced, but commonly the screening methods are based on chromatography and subsequent detection, in many cases by mass spectroscopy. A great disadvantage of the methods known in the art is that parallelization and high throughput is difficult to achieve, as the number of clones that can be analyzed is limited.

Accordingly, there is a need for new screening methods, which allow the detection of strains, which show improved properties in the production of compounds, in particular small molecules such as amino acids or sugars or intermediate chemical building blocks, but also in the production of effector molecule that may influence the growth behavior of other cells or microorganisms.

One approach was the use of biosensors for the analysis or identification of small molecules in production media. Pfleger et al. (Pfleger B F, et al.; Metabolic Engineering; 2007; 30-38) describe the generation of a *E. coli* strain, which is suitable as mevalonate biosensor and expresses GFP in the presence of mevalonate, allowing quantitative detection of mevalonate in an extracellular environment. Bertels et al. (Bertels, F. et al.; PLoS ONE; 2012; e41349) describe the development of a biosensor for amino acids, based on an auxotrophic *E. coli* strain comprising the eGFP gene. U.S. Pat. No. 9,279,139 B2 describes an *E. coli* glutamine biosensor, comprising the lux operon.

However, these methods are still limited, as they do not allow the rapid analysis of large libraries microorganism or of colonies for effector molecules that either stimulate growth of designated microorganism or inhibit its growth.

BRIEF DESCRIPTION OF THE INVENTION

The present invention aims to solve this problem by combining the traditional screening approaches with microfluidic devices, thus breaking down the analysis onto single cell level instead of cell cultures.

The invention relates to a method for the analysis of a first microorganism potentially secreting an effector compound, said first microorganism thereby having either
 i. an inhibitory effect on the cell division activity of a second microorganism or
 ii. an enhancing effect on the cell division activity of a second microorganism, the method comprising:
  a. providing a cell from a first microorganism which potentially produces an effector compound of interest and a cell from a second detector microorganism;
  b. introducing both cells into a microdroplet for incubation;
  c. introducing the microdroplet into a microfluidic system;
  d. analyzing in said microfluidic system the cell of the second microorganism for the exhibition of an enhanced growth effect or the exhibition of an inhibited growth effect stemming from said effector compound.

In another embodiment, the invention relates to a method for the analysis of a first microorganism potentially secreting an effector compound, said first microorganism thereby having either
 i. an inhibitory effect on the cell division activity of a second microorganism or
 ii. an enhancing effect on the cell division activity of a second microorganism, the method comprising:
  a. providing a cell from a first microorganism which potentially produces an effector compound of interest and a cell from a second detector microorganism;
  b. introducing both cells into separate microdroplets for incubation;
  c. bringing the first microorganism into direct contact with the second microorganism by fusing the microdroplets for incubation;
  d. introducing the microdroplets into a microfluidic system;
  e. analyzing in said microfluidic system the cell of the second microorganism for the exhibition of an enhanced growth effect or the exhibition of an inhibited growth effect stemming from said effector compound.

In yet another embodiment, the invention relates to a method for the analysis of a first microorganism potentially secreting an effector compound, said first microorganism thereby having either
 i. an inhibitory effect on the cell division activity of a second microorganism or
 ii. an enhancing effect on the cell division activity of a second microorganism, the method comprising:

a. providing a cell from a first microorganism which potentially produces an effector compound of interest and a cell from a second detector microorganism;
b. introducing the first microorganism into microdroplets for incubation;
c. bringing the first microorganism into direct contact with the second microorganism by picoinjection of the second microorganism into the microdroplets for incubation;
d. introducing the microdroplets into a microfluidic system;
e. analyzing in said microfluidic system the cell of the second microorganism for the exhibition of an enhanced growth effect or the exhibition of an inhibited growth effect stemming from said effector compound.

Various applications of such a method may be envisioned. It may be envisioned that the method additionally comprises the step of isolating the effector substance.

In one embodiment, the first microorganism and/or second microorganism is preferably a bacterial cell, fungal cell, yeast cell, algal cell, eukaryotic cell or a prokaryotic cell. One may be a bacterial cell and the other a fungal cell, one may yeast cell and the other prokaryotic cell, etc. In some embodiments they stem from the same genus, i.e. both be prokaryotes or both be eukaryotes. The prokaryotes may be bacteria or archaea.

The invention further relates to the use of the method for the analysis of a mutated microorganism, producing a compound.

DETAILED DESCRIPTION OF THE INVENTION

A first aspect of the present invention relates to a method for the identification of a first microorganism potentially secreting an effector compound, said first microorganism thereby having either
  i. an inhibitory effect on the cell division activity of a second microorganism or
  ii. an enhancing effect on the cell division activity of a second microorganism, the method comprising:
    a. providing a cell from a first microorganism which potentially produces an effector compound of interest and a cell from a second detector microorganism;
    b. introducing both cells into a microdroplet for incubation;
    c. introducing the microdroplet into a microfluidic system;
    d. analyzing in said microfluidic system the cell of the second microorganism for the exhibition of an enhanced growth effect or the exhibition of an inhibited growth effect stemming from said effector compound.

Ideally, in the above method the first microorganism is grown as a single cell in a droplet that then becomes fused with droplet that contains the test organism. Following co-culture, those droplets are selected that either show growth promotion or counter-selection of the test organism. This scheme is encompassed in step (b), wherein both cells are introduced into a microdroplet for incubation. Thus, either the two cells are directly introduced into one microdroplet or this is done by fusing a first and a second microdroplet.

In one embodiment, the method according to the present invention further comprises the step of co-culturing a cell from a first microorganism and cell from a second microorganism into a microdroplet.

Further, steps (b) and (c) may be reversed. The cells may be brought into the single microdroplet also at a time point when they are already in the microfluidic device. This is expressed also by the term method "comprising" indicating that the steps need to be performed but not necessarily in the order as shown above.

In one embodiment, the method according to the present invention additionally comprises the step of isolating the effector substance after step (c).

The invention relates to a method for the identification of a first microorganism potentially secreting an effector compound, said first microorganism thereby having an enhancing effect on the cell division activity of a second microorganism, the method comprising:
  a. providing a cell from a first microorganism which potentially produces an effector compound of interest and a cell from a second detector microorganism;
  b. introducing both cells into a microdroplet for incubation;
  c. introducing the microdroplet into a microfluidic system;
  d. analyzing in said microfluidic system the cell of the second microorganism for the exhibition of cell division activity.

In another embodiment, the invention relates to a method for the analysis of a first microorganism potentially secreting an effector compound, said first microorganism thereby having either
  i. an inhibitory effect on the cell division activity of a second microorganism or
  ii. an enhancing effect on the cell division activity of a second microorganism, the method comprising:
    a. providing a cell from a first microorganism which potentially produces an effector compound of interest and a cell from a second detector microorganism;
    b. introducing both cells into separate microdroplets for incubation;
    c. bringing the first microorganism into direct contact with the second microorganism by fusing the microdroplets for incubation;
    d. introducing the microdroplets into a microfluidic system;
    e. analyzing in said microfluidic system the cell of the second microorganism for the exhibition of an enhanced growth effect or the exhibition of an inhibited growth effect stemming from said effector compound.

In yet another embodiment, the invention relates to a method for the analysis of a first microorganism potentially secreting an effector compound, said first microorganism thereby having either
  i. an inhibitory effect on the cell division activity of a second microorganism or
  ii. an enhancing effect on the cell division activity of a second microorganism, the method comprising:
    a. providing a cell from a first microorganism which potentially produces an effector compound of interest and a cell from a second detector microorganism;
    b. introducing the first microorganism into microdroplets for incubation;
    c. bringing the first microorganism into direct contact with the second microorganism by picoinjection of the second microorganism into the microdroplets for incubation;

d. introducing the microdroplets into a microfluidic system;
e. analyzing in said microfluidic system the cell of the second microorganism for the exhibition of an enhanced growth effect or the exhibition of an inhibited growth effect stemming from said effector compound.

Herein, cell division is defined reproduction or killing of a prokaryotic, eukaryotic, fungal cell, yeast cell, as germination of spores or an increase in size of the cell.

Herein, enhanced cell division activity may be the increase in number of cells or is measured by an increase in absorbance, turbiometry or fluorescence or luminescence that is caused by the expression of suitable reporter genes by the microorganism.

The invention relates to a method for the identification of a first microorganism potentially secreting an effector compound, said first microorganism thereby having an inhibitory effect on the cell division activity of a second microorganism, the method comprising the steps of
a. providing a cell from a first microorganism which potentially produces an effector compound of interest and a cell from a second detector microorganism;
b. introducing both cells into a microdroplet for incubation;
c. introducing the microdroplet into a microfluidic system;
d. analyzing in said microfluidic system the cell of the second microorganism for the exhibition of an inhibited growth effect stemming from said effector compound.

Herein, inhibited growth effect may be the absence of spore germination, the maintenance of the average cell number, the killing of cells or is measured by a stable absorbance, turbiometry, fluorescence or luminescence signal or a decrease absorbance, turbiometry, fluorescence or luminescence signal that is caused by the expression of suitable reporter genes by the microorganism.

The method is suitable for any kind of microorganism, which can be handled on single cell level. The microorganism which produces a compound (first) and the detector microorganism (second) might be of the same species or different species.

In one embodiment, said first microorganism is from a natural sample suspected of comprising microorganisms that produce the desired effector substance or wherein the sample is from a variant strain pool generated by random mutagenesis.

The method is particularly suitable for the analysis of microorganisms which had been mutated or genetically engineered in order to optimize the production of desired compounds. In one embodiment of the invention, the microorganism which produces a compound is therefore a mutated or genetically engineered organism.

Mutated or genetically engineered organisms can be generated by means known to the person skilled in the art. Sample methods to induce mutations in microorganisms include but are not limited to, exposure to radiation, in particular UV-radiation or radioactive radiation, stress, phages and viruses, transposon mutagenesis, homologous recombination, metabolic engineering, or chemical mutagenesis. Alternatively, the microorganism producing a compound may comprise a plasmid or cosmid comprising a modified or mutated enzyme or biosynthesis pathway.

Suitable microorganisms, which might be mutated or produce a compound include, but are not limited to bacterial strains, archeal strains, fungal strains, yeast strains, algae, plant protoplasts, prokaryotic or eukaryotic cells, spores, insect cells or insect strains. In a preferred embodiment of the invention, the microorganism which produces a compound of interest is a bacterial strain, a fungal strain or yeast strain. In a most preferred embodiment the microorganism which produces a compound, is a bacterial or fungal strain.

In a preferred embodiment of the invention, a library of microorganisms producing a compound of interest is generated and analyzed. The method of the invention is in particular suitable for screening for microorganisms exhibiting a higher productivity of the compound and a higher final titer of the compound in a library of microorganisms.

The produced compound of interest might be any compound, which can be exported or secreted into the medium by the microorganism and which can be detected by the detector microorganism (second). The compound preferably has either direct commercial value or may serve as an intermediate in the production of a further compound, which has commercial value.

In one embodiment, suitable effector compounds include, but are not limited to, primary metabolites: L- and D-amino acids; sugars and carbon sources such as L-arabinose, N-acetyl-D-glucosamine, N-acetyl-D-mannosamine, N-acetylneuraminate, lactose, D-glucosamine, D-glucose-6-phosphate, D-xylose, D-galactose, glycerol, maltose, maltotriose, and melibiose; nucleosides such as cytidine, guanine, adenine, thymidin, guanosine, adenosine; lipids such as hexadecanoate and glycerol 3-phosphate; indole, maltohexose, maltopentose, putrescine, spermidine, ornithine, tetradecanoate and nicotinamide adenine dinucleotide.

Further relevant compounds of interest include, but are not limited to, secondary metabolites. Such metabolites can be produced naturally by the producer microorganism but may also be generated via a heterologous biosynthetic pathway introduced into the microorganisms by genetic engineering. Examples of secondary metabolites include, but are not limited to, polyketides (such as erythryomycin and avermectins), small molecules (such as resveratrol, steviol, and artemisenin) or non-ribosomal peptides.

The detector microorganism may also be any organism that can be handled on single cell level. Suitable microorganisms, which might be mutated or genetically engineered, include, but are not limited to, bacterial strains, archeal strains, fungal strains, yeast strains, algae, plant protoplasts, prokaryotic or eucaryotic cells, spores, insect cells or insect strain.

Preferably, the detector strain which shows either enhanced or reduced growth is a different microorganism than the strain producing a compound.

For example, the method allows for the selection of bacterial strains from a) natural samples (e.g. soil microbiome, human microbiome), or b) bacterial strain variant pools (e.g. using a single defined target strain from which variants are created by UV random mutagenesis, chemical mutagenesis, transposons) that exert either a growth inhibition or growth promoting activity on a specific target organism.

Examples are:

Bacterial strains that promote growth of plants (biofertilizers);

Bacterial strains that inhibit growth of pathogens (plant pathogens, human pathogens, animal pathogens—biofungicides, bioinsecticides, bioherbicides, biological preservatives (strains) for dairy and other food products, strains that prevent overgrowth of specific pathogens like *Staphylococcus aureus*);

Bacterial strains that promote a "balanced" microbiota, i.e. they do not completely prevent growth of other microorganisms but create an environment where all strains are at a healthy equilibrium (areas such as immune health, digestive health, skin care);

Bacterial strains that act as antimicrobials that can be used to replace antibiotics in therapy/prevention or for growth promotion in animal live stock.

The second microorganism is a specific organism by means of which the effect (e.g. growth inhibition or growth promotion, antimicrobial activity) can be tested. Such model organism might be engineered to create a measurable signal, i.e. it might express a gene whose activity can be measured by means of a fluorescent signal or an enzyme activity that can be measured by increase of decrease of an enzyme/substrate correlated signal (enzyme activity or enzyme inhibition).

The effector organism is, for example, a bacterial strain that exerts such desired effect on the test organism. The effector organism is commonly derived from a huge pool of different species as they either occur in natural samples or in bacterial strain variant pools.

Herein, analyzing in said microfluidic system the cell of the second microorganism for the exhibition of an enhanced growth effect or the exhibition of an inhibited growth effect stemming from said effector compound means, for example, directly or indirectly detecting cell division, directly or indirectly detecting cell cycle arrest, directly or indirectly detecting gene expression of a cell cycle inhibitor gene, such as Cip or kip (CDK interacting protein/Kinase inhibitory protein) family and the INK4a/ARF (Inhibitor of Kinase 4/Alternative Reading Frame) family, prevent the progression of the cell cycle. Because these genes are instrumental in prevention of tumor formation, they are known as tumor suppressors.

The cip/kip family includes the genes p21, p27 and p57. They halt cell cycle in G1 phase, by binding to, and inactivating, cyclin-CDK complexes. p21 is activated by p53 (which, in turn, is triggered by DNA damage e.g. due to radiation). p27 is activated by Transforming Growth Factor of β (TGF β), a growth inhibitor.

The INK4a/ARF family includes p16INK4a, which binds to CDK4 and arrests the cell cycle in G1 phase, and p14ARF which prevents p53 degradation.

One may detect directly or indirectly mitosis, DNA replication, spindle formation, transcription factors involved in the cell cycle phases or arrest.

In one embodiment, cell division is detected by means of a recombinant gene expressing a label, that may be detected, wherein the number of cells in the droplet expressing the label is linearly proportionally equivalent to the amount of label that is detectable.

In a preferred embodiment, the detectable signal is a fluorescent signal. In one embodiment, said fluorescent signal is generated by the reporter gene product or the reporter gene operon. In a preferred embodiment the reporter gene encodes a fluorescent protein such as green fluorescent protein (GFP), a variant of GFP, yellow fluorescent protein (YFP), a variant of YFP, red fluorescent protein (RFP), a variant of RFP, cyan fluorescent protein (CFP), a variant of CFP or the reporter gene operon is a luminescence operon such as the lux operon. It is known to the person skilled in the art that homologs of said proteins may be used.

One further possibility is the use of modified allosteric transcription factors as described by Taylor et al. (Taylor, N. D, et al.; Nature Methods, Vol. 13; 2016; 177-183) or the use of synthetic biosensors as described by Rogers et al. (Rogers, J. K. et al.; Nucleic Acids Research; 43; 2015; 7648-7660).

An alternative preferred detector strain might be auxotrophic for the compound, i.e. the detector strain cannot survive without an exogenous supply of said compound. In this case, the reporter gene might be continuously activated.

A detector microorganism which is auxotrophic for compound A is unable to grow unless compound A is present in the culture medium. Such a microorganism could be generated via knockout of one or more genes in said microorganism. In the absence of these genes, the microorganism would be unable to synthesize compound A. In some cases, compound A is required directly for growth. In other cases, compound A serves as an intermediate for the synthesis of compound B, which is required for growth. Preventing the synthesis of compound A therefore precludes the synthesis of compound B and prevents cell growth.

Methods to generate auxotrophic microorganisms are known to the person skilled in the art. Suitable methods include the generation of knockout mutants or random mutagenesis. Alternatively, several naturally existing microorganisms are auxotrophic for specific compounds. In most cases said microorganisms are auxotrophic for amino acids.

If genome-scale models are available, the compounds which may be sensed and the corresponding gene knockouts which must be made to achieve auxotrophy may be determined based on a computational optimization problem formulated around the available genome-scale model (e.g., Tepper et al. (2011), "Computational design of auxotrophy-dependent microbial biosensors for combinatorial metabolic engineering experiments" PLOS ONE 6:1).

Gene knockouts may be achieved via a variety of methods, including but not limited to homologous recombination, gene inactivation via PCR products (e.g., Datsenko and Wanner (2000), "One-step inactivation of chromosomal genes in *Escherichia coli* K-12 using PCR products" PNAS 97(12):6640-6645), CRISPR-Cas9, transposon mutagenesis and phage transduction. Thus, auxotrophic sensor strains can be generated today with little effort and time required.

Generated auxotrophic microorganisms may also be engineered to express a reporter molecule, which may be a fluorescent protein (green fluorescent protein or its derivatives such as eGFP, red fluorescent protein or its derivatives such as mCherry, cyan fluorescent protein or its derivatives, yellow fluorescent protein or its derivatives) or an operon of genes whose expression results in luminescence (such as the lux operon). In a preferred embodiment, generated auxotrophic microorganisms are also engineered to express a reporter molecule, which may be a fluorescent protein (green fluorescent protein or its derivatives such as eGFP, red fluorescent protein or its derivatives such as mCherry, cyan fluorescent protein or its derivatives, yellow fluorescent protein or its derivatives) or an operon of genes whose expression results in luminescence (such as the lux operon).

The cultivation of microorganisms is known to the person skilled in the art. In general, microorganisms are cultivated in a liquid medium or on a solid medium. In general, solid media are based on liquid media.

Prior to analysis the cells might be cultured in any suitable culture medium. Suitable culture media are dependent on the microorganisms. The person skilled in the art generally differentiates between undefined media, such as for example LB-medium and defined media, in particular minimal media, such as M9 minimal medium or MOPS minimal medium.

Undefined media usually comprise water, a carbon source, a protein and nitrogen source and salts. In general, the carbon, protein and nitrogen source can be an extract, for example, of yeast and/or beef extract or protein hydrolysates, such as tryptone or peptone. The exact amino acid composition and salt concentration or composition is usually unknown.

Defined media on the other hand are exactly known. In a defined medium, all used chemicals are known and the concentrations of the other compounds are known. In the specific case of minimal media, the medium contains the minimum nutrients possible for colony growth, generally without the presence of amino acids.

As not every organism is able to grow in any medium, it is necessary to adapt the selected medium to the types of microorganisms used. For analysis, a medium which allows survival of both microorganisms is necessary. Depending on the selected microorganisms, the person skilled in the art will know and be able to select the right growth medium.

Accordingly, the method is not suitable for every combination of microorganisms. It is, for example, not possible to cultivate a microorganism requiring a medium with high salt concentration together with a microorganism requiring a low salt concentration. Therefore, the detector microorganism needs to be selected dependent on the microorganism producing a compound.

Preferably, prior to the analysis according to the method of the invention, the microorganisms are cultivated separately in appropriate media. In one embodiment of the invention, the microorganisms are cultivated and incubated in full media. In an alternative embodiment, the microorganisms are cultivated in defined media, preferably minimal media.

In an alternative embodiment of the invention, the microorganism producing a compound is cultivated in a full medium and the detector microorganism is cultivated in a defined medium, preferably cultivated in a minimal medium.

For analysis the microorganisms are then used in their respective medium or transferred in an analysis medium. Preferably, said analysis medium is a defined medium. In a more preferred embodiment, said analysis medium is a minimal medium.

The person skilled in the art knows how to transfer cell cultures in different media. In one embodiment, the different culture media are simply mixed to form a new culture medium. In a preferred embodiment, the microorganisms are transferred using several centrifugation and washing steps, involving suspending the cells in the target medium.

Microorganisms in the analysis media are then diluted and/or encapsulated into single droplets. Droplet generation is known to the person skilled in the art. Preferably, said droplets are generated using a microfluidic device. Preferably, during droplet generation the microorganism producing a compound and the detector microorganism are combined. Alternatively, the microorganism producing a compound and the detector strain are diluted into separate droplets and two droplets, each comprising one of the microorganisms are united into a single droplet.

Regardless of the method of droplet generation, it is preferred that the final droplets in their majority comprise at least one microorganism of each type, i.e. at least one microorganism producing a compound and at least one detector microorganism. Preferably, the majority of droplets comprises one cell of each microorganism.

It is essential that the droplets additionally comprise all necessary compounds to support growth of the microorganisms, both the detector microorganism and the microorganism producing a compound, and to support the production of said compound by the producing microorganism.

The droplets comprising the microorganisms may be additionally encapsulated to separate the contents from the environment. A possible method of encapsulation is discussed in WO 2010/063937 A1. In a preferred embodiment, the droplets are encapsulated in a soft alginate shell.

Alternatively, the droplets are separated from the environment using a phase immiscible with the medium to separate or encapsulate droplets. In one embodiment said immiscible phase is an oil. In a more preferred embodiment, said immiscible phase is a fluorinated oil.

In one embodiment, the droplets have a volume of between 1 pL and 1 µL.

After diluting and optionally encapsulating the droplets, the microorganisms are incubated for an appropriate amount of time. Said incubation might be performed directly in the microfluidic device or separate from the microfluidic device.

In one embodiment, the incubation is performed in the microfluidic system.

Incubation might be performed in any way possible. It is however important that the droplets remain intact during the incubation. Stable droplets might be incubated outside of a microfluidic device and later again be subjected to a microfluidic device.

Independently from where the droplets and microorganisms are incubated, it is preferred that the microorganisms are incubated at appropriate temperatures. The suitable temperature is dependent on the microorganisms in the droplets and the requirements for the production of the compounds. For example, bacterial cultures, such as *E. coli* usually require temperatures between 20 and 37° C.

In one embodiment, the incubation temperature is between 18° C. and 50° C. In a preferred embodiment, the incubation temperature is between 20 and 48° C. In a more preferred embodiment, the incubation temperature is between 25 and 45° C. In an even more preferred embodiment, the incubation temperature is between 35 and 40° C. In the most preferred embodiment, the incubation temperature is 37° C.

The temperature may vary during incubation or may be constant. In one embodiment of the invention, the droplets comprising the microorganisms are incubated at a constant temperature. In an alternative embodiment, the droplets comprising the microorganisms are incubated at variable temperatures.

Incubation time has to be selected accordingly. In general, the incubation time needs to be long enough to allow for the microorganisms to grow and produce and detect the compound. The time is dependent of the medium, the temperature and the microorganisms. A "richer" medium and a temperature near the optimum temperature for the microorganism results in shorter incubation times.

After incubation, the droplets are analyzed in a microfluidic device, screening for the activation of the reporter gene. The detection method is dependent on the reporter gene. If the reporter gene is a fluorescent protein or a reporter operon generating a fluorescent signal, the detection method is fluorescence detection.

Preferably, following incubation, the concentration of the reporter molecule in each droplet is determined via fluorescence or luminescence measurements. Such measurements may be performed on the same microfluidic device in which the droplets were generated or on a second microfluidic device distinct from the first microfluidic chip. Preferably, improved production strains can be identified by fluorescence or luminescence above that measured from droplets produced by co-encapsulating the biosensor strain with the parent production strain.

After detection, the droplets which had been identified as comprising an activated reporter gene or a surviving detector microorganism are selected and separated for further analysis. Potential mechanisms for sorting the droplets are known to the person skilled in the art. In one embodiment, the cells are sorted using dielectrophoresis. In another embodiment, the cells are sorted using acoustic waves. In yet another embodiment, the cells are sorted using FACS.

In one embodiment, the droplets comprising at least one cell of each medium are generated by generating a droplet comprising at least one cell of a first microorganism and in said chamber picoinjecting said second microorganism into said droplet (see FIG. 6).

In an alternative embodiment, the droplets are generated by generating droplets comprising a first microorganism and droplets comprising the second microorganism and combining and/or fusing the droplets into single droplets in the chamber.

In a second aspect, the invention disclosed herein relates to microorganism or effector compound identified by means of the method according to the first aspect and its embodiments.

Examples

To identify bacterial strains that prevent excessive growth of the yeast-like fungus Malassezia spec that is one of the potential causes for Dandruff, a scalp microbiota sample is washed with an isotonic buffer to recover bacteria present in the sample. These bacteria are then diluted using a chemically defined medium, generating a library of potential effector organisms.

A strain of Melassezia that is modified to express the coding sequence of a fluorescent protein (e.g., GFP, eGFP, mCherry, RFP, etc.) is grown in one pool of droplets. The proliferation of this strain can be monitored via fluorescence measurements, namely illuminating the cells with light of a wavelength or range of wavelengths and measuring the amount of light emitted by the cells at a wavelength or range of wavelengths greater than the wavelength(s) used for illumination. This Malassezia strain will be referred to hereafter as the "test organism" (the second microorganism).

The natural bacteria present in the scalp microbiota are diluted to become encapsulated on the level of single cells into a second pool of droplets. They are collectively called the "effector organism" (said first microorganism).

Microfluidic droplets 20 pL in volume are generated using a microfluidic system in which the aqueous phase comprising the library of effector organisms and of the test organism diluted in a chemically defined medium is separated into droplets by a fluorinated oil (e.g., HFE7500) containing a fluorinated surfactant. These microfluidic droplets pools are collected and incubated for growth or are directly subjected to droplet fusion, mixing the test organism with the effector organism in each individual droplet and subjecting them to co-culture conditions. Alternatively, droplets of the effector organisms are subjected to picoinjection, in which a small, defined volume (5 pL) of test organism culture is added to each microfluidic droplet, thereby contacting cells of the effector organism with cells of the test organism within microfluidic droplets. The picoinjected droplets are then collected and incubated at 30° C. to allow for growth of the effector organism, that through production and secretion of certain compounds affects the subsequent growth of the test organism, and concomitant production of the fluorescent protein.

The microfluidic droplets are then analyzed using the microfluidic system. The fluorescence of each droplet is analyzed by illuminating the droplet with a laser having a wavelength corresponding to the excitation maximum of the fluorescent protein of interest and measuring the amount of light emitted by the droplet at a range of wavelengths longer than the wavelength used for illumination/excitation. Droplets exhibiting higher fluorescence must contain higher concentrations of fluorescent protein and must therefore contain a higher number of cells of the test organism. One may also infer that droplets containing higher numbers of test organism cells must also contain effector organism cells that do not interfere with the growth of the test organism cells. Conversely, droplets exhibiting a lower fluorescence must contain a lower concentration of fluorescent protein and must therefore contain a lower number of cells of the test organism. In this case, one might also infer that droplets containing lower number of test organism cells must also also contain effector organism cells that do interfere with the growth of the test organism cells.

Using the microfluidic system, droplets exhibiting low levels of fluorescence are separated from the remainder of the droplet pool and collected. These droplets are then spread on solid media, which is then incubated to recover effector organisms which exhibit a growth arresting effect or killing effect on the test organism. Individual clonal isolates are then analyzed in a secondary screen to confirm growth inhibition on the test organism: colonies are inoculated into appropriate medium and are cultured for several days, and their impact on growth inhibition on Melassezia is tested under various conditions.

The invention also relates to a microorganism or effector compound identified by the method according to the invention.

Experimental Rationale

To demonstrate the microbial selection system using microfluidic emulsions, two different microorganisms were employed. To be able to grow and divide, one microorganism requires a compound that the second organism produces. The first microorganism is a tryptophan auxotroph *S. cerevisiae* strain CLIB339. This strain grows well in growth medium containing the full complement of amino acids but does not grow without tryptophan. The second microorganism is a strain of *E. coli* which contains a plasmid overproducing tryptophan. The first microorganism, auxotrophic *S. cerevisiae*, was tested whether it grows when in the presence of the tryptophan producing *E. coli* strain. To be able to detect the growth of the *S. cerevisiae*, a gene expressing mCherry protein was introduced, thus rendering the yeast fluorescent. The fluorescence is easily detectable in droplets on a microfluidic platform and can serve as proxy for the production of biomass (i.e. growth and division) of the *S. cerevisiae* strain.

Cloning of the Gene Responsible for the Expression of mCherry into *S. cerevisiae*

Cloning of mCherry into the Plasmid pD1217 and Transformation of *S. cerevisiae*

The gene responsible for the expression of mCherry was amplified from pRFSD-mCherry (see Table 1), with addition of SapI restriction sites to the extremities of the amplicon. The PCR product and pD1217 (see Table 1) were then digested by SapI and ligated together. The ligation was then transformed into *E. coli* DH5α and grown overnight at 37° C. on Luria Bertani (LB) agar plates supplemented with 33 µg/mL kanamycin. The plasmid construct was verified by restriction digest. The resulting plasmid, named pD1217-mCherry, was subsequently transformed into *S. cerevisiae* CL1B339 (see Table 1) giving CLIB339 (pD1217-mCherry).

Transformation of *Escherichia coli* with Plasmid Overproducing Tryptophan

*E. coli* strain DH5alpha was transformed with the plasmid pSC101-trp.I15 (see Table 1) and the transformants were selected on media containing 10 µLg/mL tetracycline.

TABLE 1

Strains, plasmids and primers used

| | Genotype and properties | |
|---|---|---|
| Strains | | |
| *E. coli* DH5α | fhuA2 Δ(argF-lacZ)U169 phoA glnV44 Φ80 Δ(lacZ)M15 gyrA96 recA1 relA1 endA1 thi-1 hsdR17 Used for Cloning | New England Biolabs |
| *S. cerevisiae* CLIB339 | Mat a, ura3-52, leu2-112, his3, trp1-289 | CIRM-INRA |
| *S. cerevisiae* CLIB339 (pD1217-mCherry) | Mat a, ura3-52, leu2-112, his3, trp1-289 Transformed with pD1217 inserted with mCherry | This study |
| *Escherichia coli* (Migula) Castellani and Chalmers/ pSC101-trp.I15 | F' traD36 proA+ proB+ laclq delta(lacZ)M15 delta(lac-proAB) supE thi-1 lambda- Transformed with pSC101-trp.I15 plasmid, inserted with the tryptophan operon | ATCC |
| Plasmids and primers | | |
| pRFSD-mCherry | 88 ng/mL in MiliQ | Internal |
| pD1217 | Yeast expression vector, Kanamycin resistance gene | ATUM |
| pD1217-mCherry | mCherry yeast expression vector, Histidine | This study |
| Primers | | |
| ForPrim Vec InsertSapI | tacacgtacttagtcgctgaagctctt ctatgGTGAGCAAGGGCGAGGAG | This study |
| RevPrim Vec InsertSapI | taggtacgaactcgattgacggctctt ctaccCTAAAGCTTGTACAGCTCGTC | This study |

Co-Culture of *S. cerevisiae* CLIB339 (pD1217-mCherry) and *Escherichia coli* (pSC101-trp.I15) in Water in Oil Emulsions Fabrication of Flow Focusing Devices (FFD)

Poly-(dimethylsiloxane) (PDMS) microfluidic FFDs were fabricated from 21 or 30 µm molds. The molds were produced by photolithography technique. The FFD was designed using AutoCad and printed onto photomasks. The photomasks were transferred onto a coated glass wafer by use of negative photoresist SU8-2015 or SU8-2025 to produce master molds of heights 21 and 30 µm respectively.

PDMS and a cross-linker were mixed at a 10:1 ratio, poured on to master mold, degassed and cured overnight at 70° C. The PDMS slabs were then peeled off the master molds, 0.75 µM holes punctured into the inlets and outlets of the device, bonded by plasma treatment onto glass slides and baked for 5 min at 90° C.

Wettability Modification of FFDs

To render a chip hydrophobic 1% w/w trichloro(1H,1H,2H,2H-perfluorooctyl)silane in 3M HFE7500 was flushed into the outlet channel of the PDMS chip to fill the entire channel. The solution was then removed using N2 gas.

Microbial Suspension

*E. coli* (pSC101-trp.I15) and *S. cerevisiae* CLIB339 (pD1217-mCherry) were grown separately in DOMT medium supplemented with 20 µL/mL tetracycline at 37° C. and DOMT medium supplemented with 20 µL/mL tetracycline and 76 µg/mL tryptophan respectively at 37° C. for 2 days. 2 mL of *S. cerevisiae* CLIB339 (pD1217-mCherry) was harvested and washed with PBS pH 7.2, three times by centrifugation at 3000 g for 3 minutes. The cells were resuspended in DMOT with 20 µL/mL tetracycline.

Three samples were prepared for droplet encapsulation:
1) Positive control—1 mL of *S. cerevisiae* CLIB339 (pD1217-mCherry) in DMOT supplemented with 20 µL/mL tetracycline and 76 µg/mL tryptophan,
2) Negative control—1 mL of *S. cerevisiae* CLIB339 (pD1217-mCherry) in DMOT supplemented with 20 µL/mL tetracycline, and
3) Test sample—1 mL of *E. coli* (pSC101-trp.115) and *S. cerevisiae* CLIB339 (pD1217-mCherry) in co-culture in DMOT supplemented with 20 µL/mL tetracycline.

The yeast from the original culture was added to the positive control sample to a concentration of $1.6 \times 10^7$ cells/mL, yeast from the washed sample were added to the sample to the same concentration in the test and negative control samples. *E. coli* (pSC101-trp.115) was also added to a concentration of $1.6 \times 10^7$ cells/mL.

7-amino-4-methyl-3-coumarinylacetic acid was added to concentration of 50 µM in the positive control sample, 250 µM in the test sample and 1250 µM in the negative control sample to mark the different droplet populations.

Water in Oil Emulsions with or without *E. coli* (pSC101-trp.I15)

The yeast and co-culture suspensions described above were flown into separate FFD (FIG. 9) and cut by an oil phase composed of HFE7500, 2.5% w/w surfactant (RAN biotechnologies) to produce 20 pL water in oil droplets. All droplets were collected in the same vial and incubated overnight at 37° C. 4 million droplets for each suspension were collected.

The next day, the droplets were analyzed in a reinjection device (FIG. 9) where the droplets were spaced using HFE 7500. A 375 nm laser and 561 nm laser were focused on the droplets in the channel. Fluorescence emissions were collected with 407-497 nm and 545-613 nm fluorescence filters linked to photomultiplier tubes (PMTs). The signal produced by the PMTs was processed using a data-acquisition program for statistical analysis to link the amount of droplet marker fluorescence to the amount mCherry fluorescence (as a proxy for S. cerevisiae growth) for all three conditions. The droplets showing positive mCherry fluorescence were separated into 3 populations according to their PMT1 fluorescence. The populations were then compared to observe if the presence of E. coli (pSC101-trp.I15) in droplets enriches the population of droplets containing significant biomass of S. cerevisiae CLIB339 (pD1217-mCherry) as indicated by mCherry fluorescence.

Co-Culture of S. cerevisiae CLIB339 (pD1217-mCherry) and Escherichia coli (pSC101-trp.I15) in Water in Oil Emulsions Approximatively 3.7 million droplets were processed using the data-acquisition program. PMT3 positive droplets represent positive mCherry fluorescence and the presence of S. cerevisiae CLIB339 (pD1217-mCherry) inside the droplets. This is represented on the y-axis in FIG. 10. The droplets delimited by the rectangle and marked by "test" are the droplets containing both S. cerevisiae CLIB339 (pD1217-mCherry) and E. coli (pSC101-trp.I15), while the droplets delimited by the rectangle marked by the "-" sign contained only S. cerevisiae CLIB339 (pD1217-mCherry) in a medium devoid of tryptophan.

As can be seen from FIG. 10, droplets having a significant mCherry signal detectable on PMT3 (y-axis) are present in the test sample but not in the negative control sample. Since mCherry florescence is used as a proxy for the growth of S. cerevisiae, this indicates that the yeast grows only in co-culture with the transformed E. coli strain secreting tryptophan thus demonstrating synergistic interactions between these two microorganisms through a secreted compound.

Figure 1:
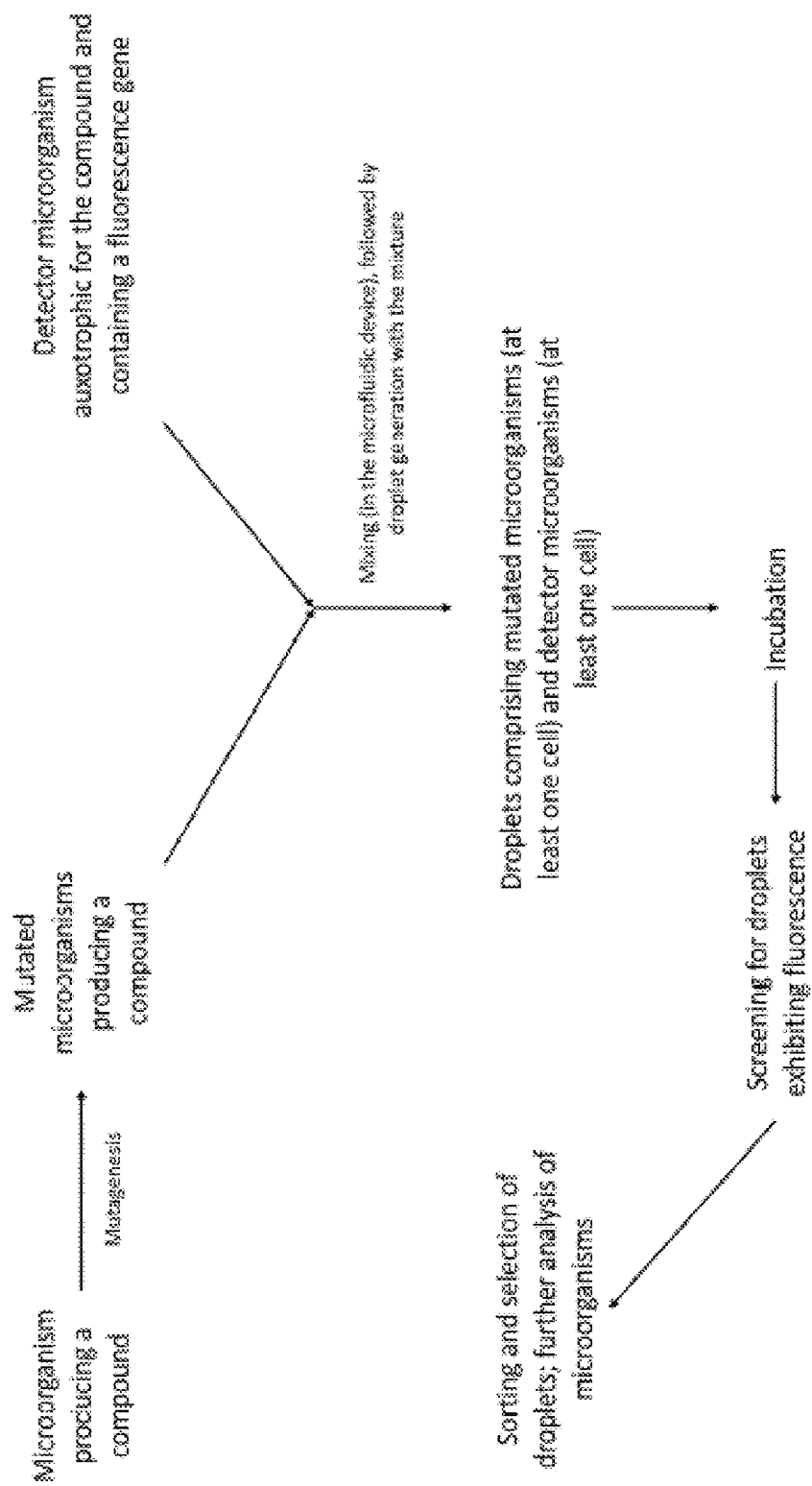
FIGS. 1 to 3 show schematic examples of preferred workflows of the method.
Figure 2:
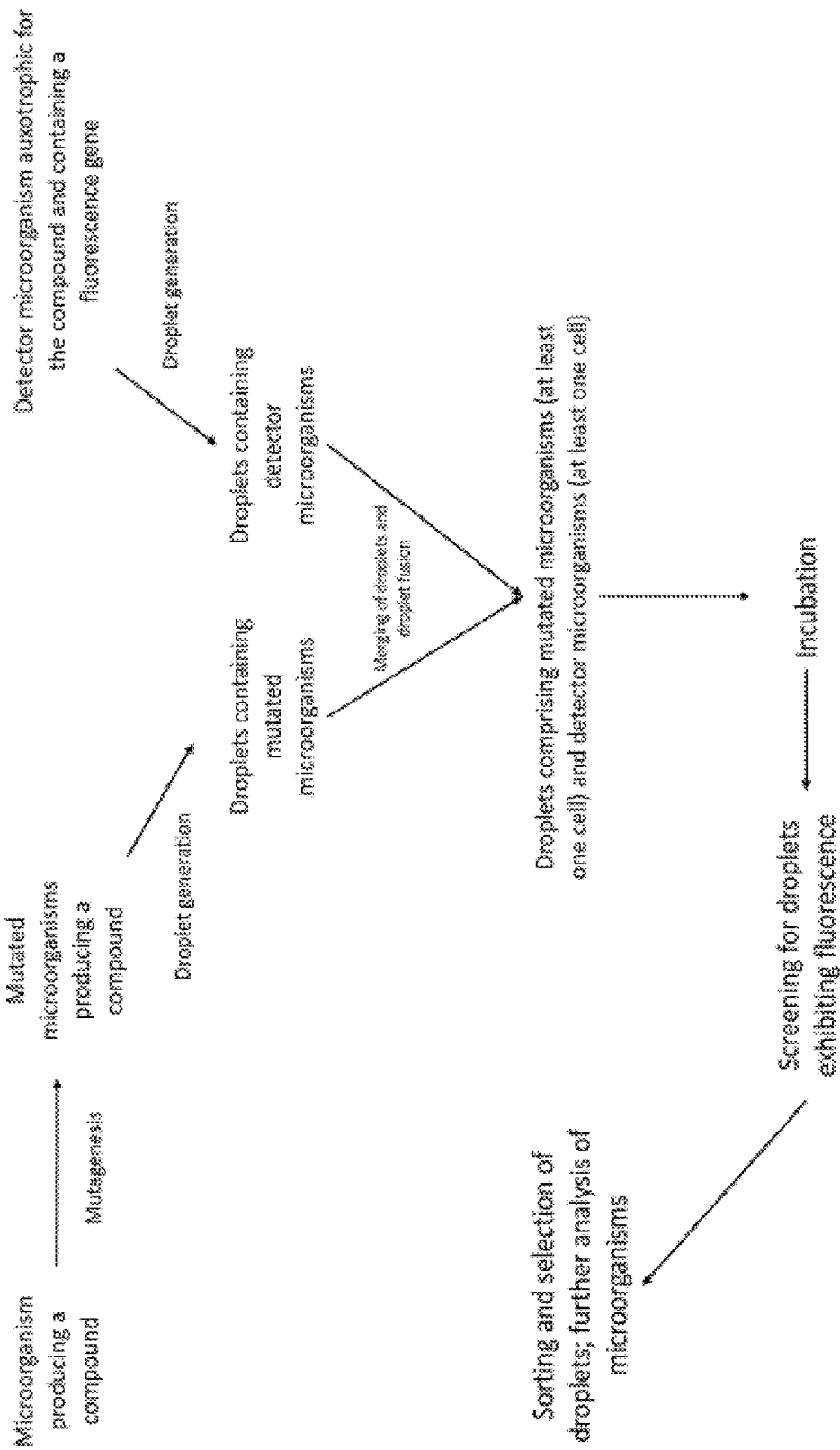
Figure 3:
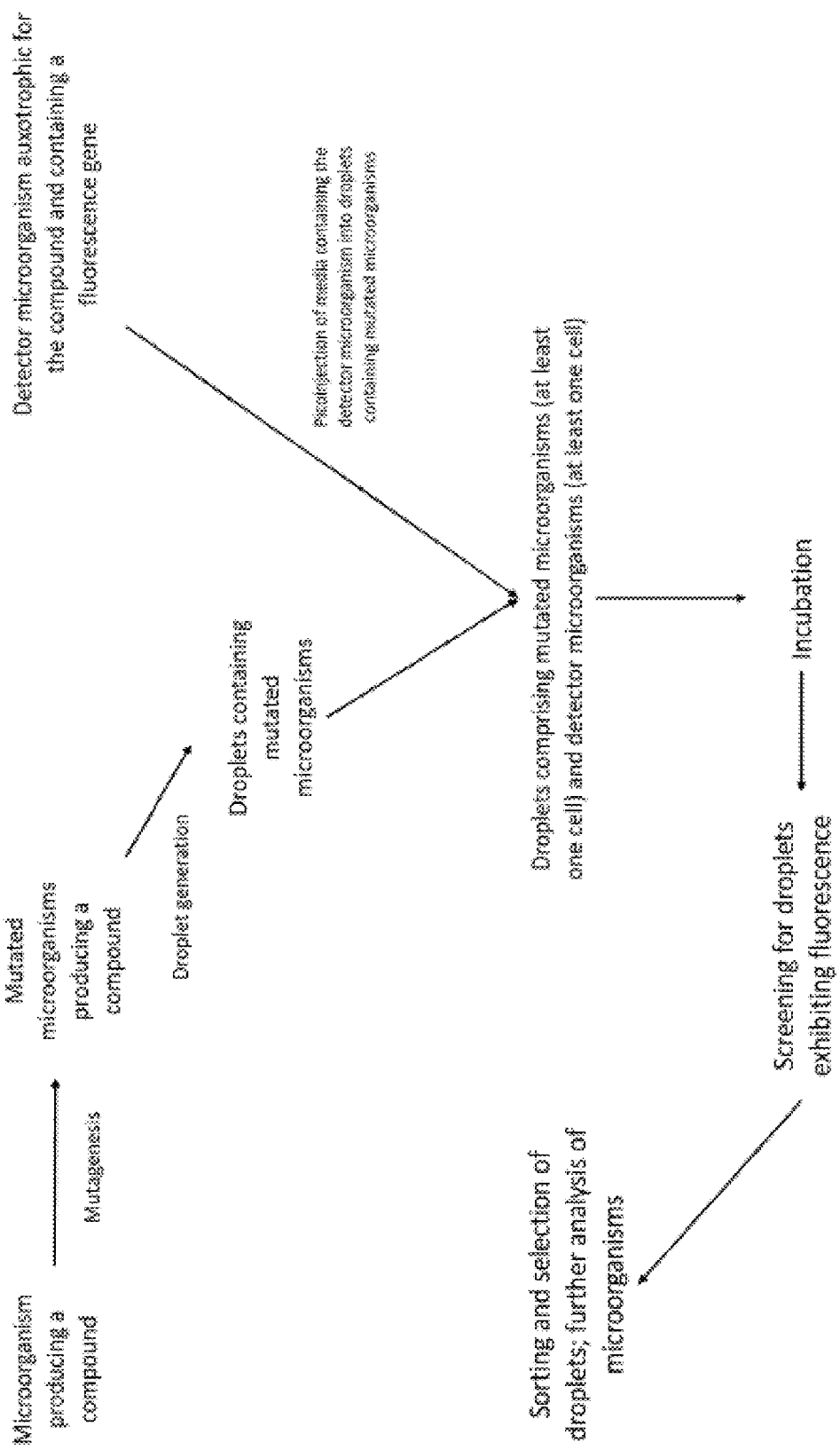
Figure 4:
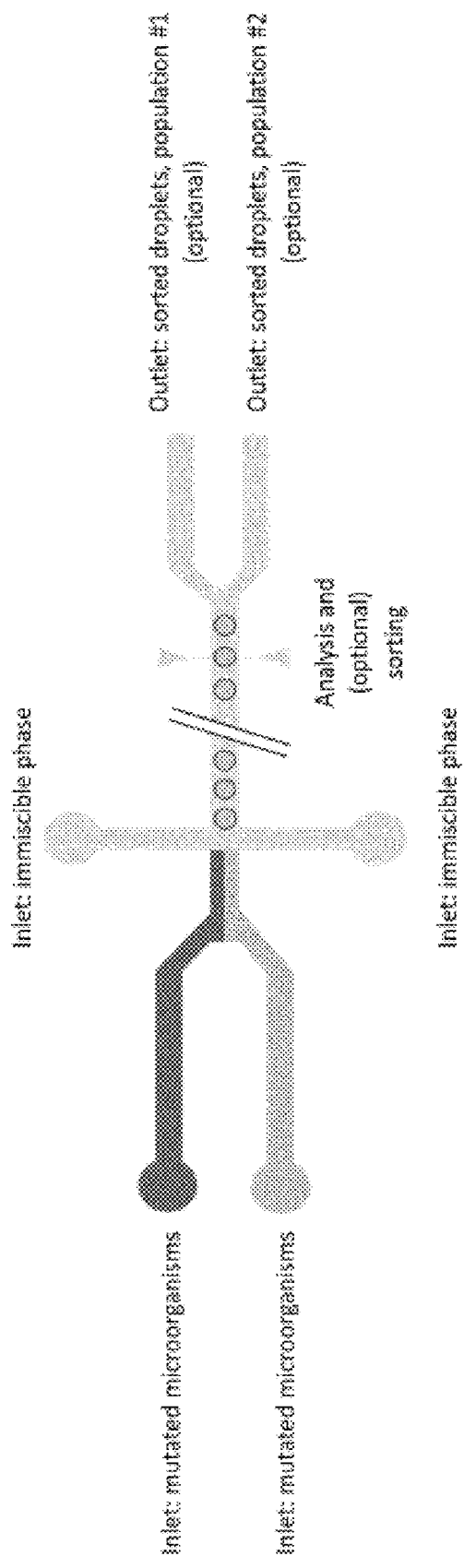
FIGS. 4 to 6 show schematics of microfluidic devices for droplet generation. Broken lines represent positions, where the droplets might be further processed either within or of the microfluidic device.
Figure 5:
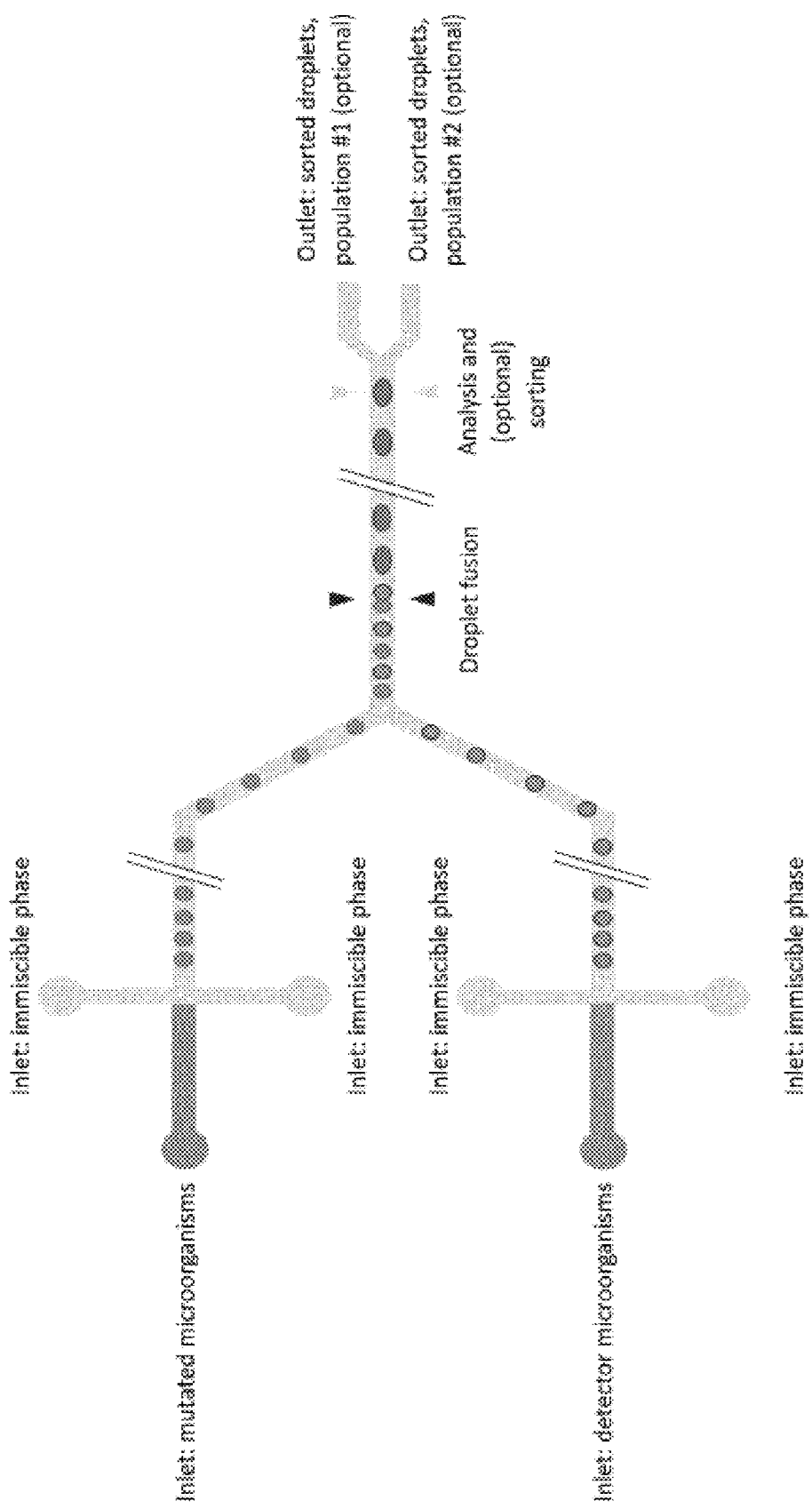
Figure 6:
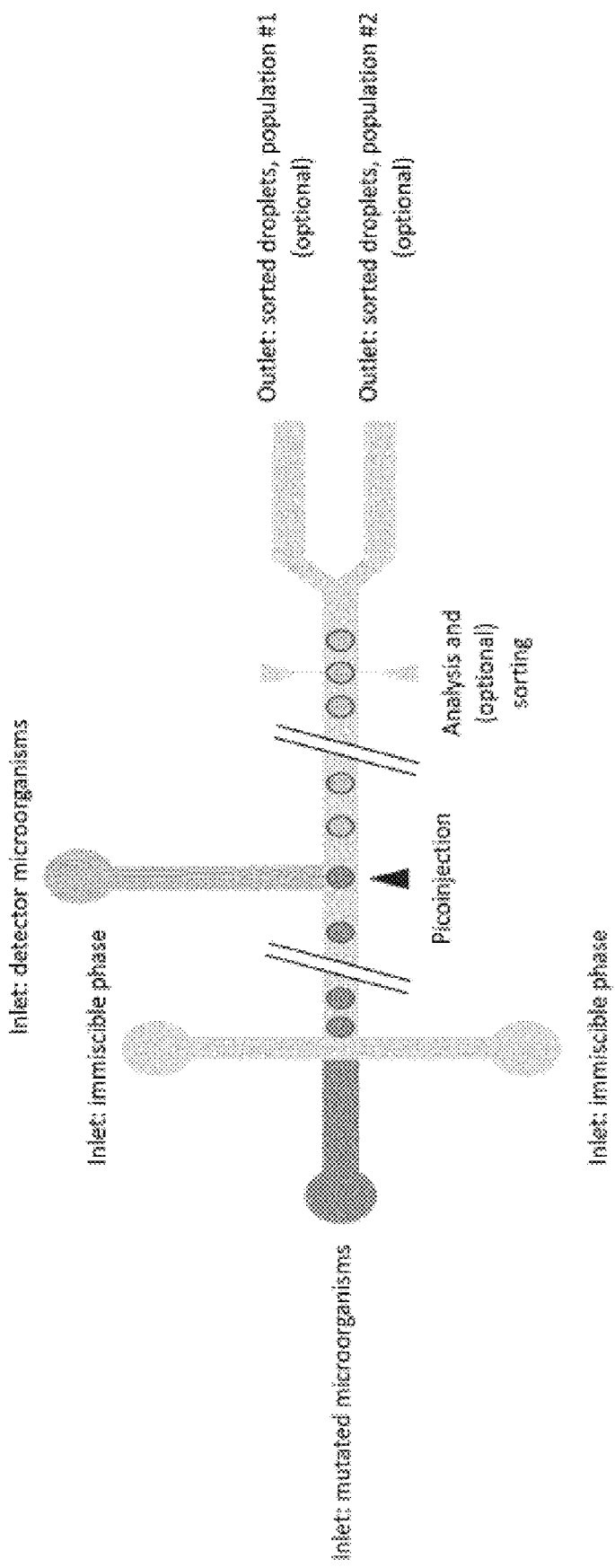
Figure 7:
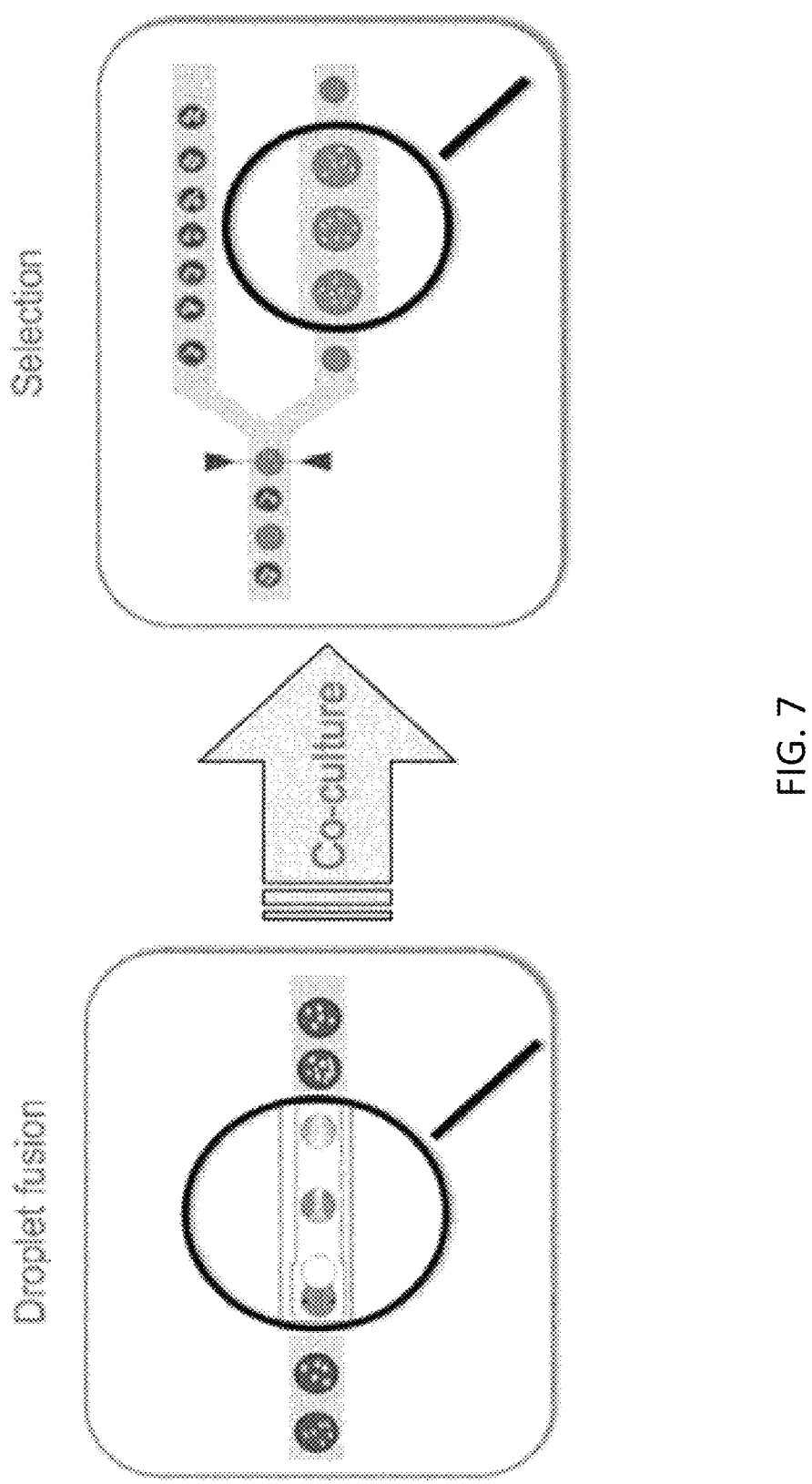
FIG. 7 shows selection of natural strains that either promote growth of a model organism or inhibit its growth is an important selection parameter, i.e. for the identification of strains that show antimicrobial or antifungal activity or in contrary, promote the growth of other a specific organism. This is achieved by separate growth of the microbiota as single cells in droplets that then become fused with droplets that contain the test organism. Following co-culture, those droplets are selected that either show growth promotion or counter-selection of the test organism.
Figure 8:
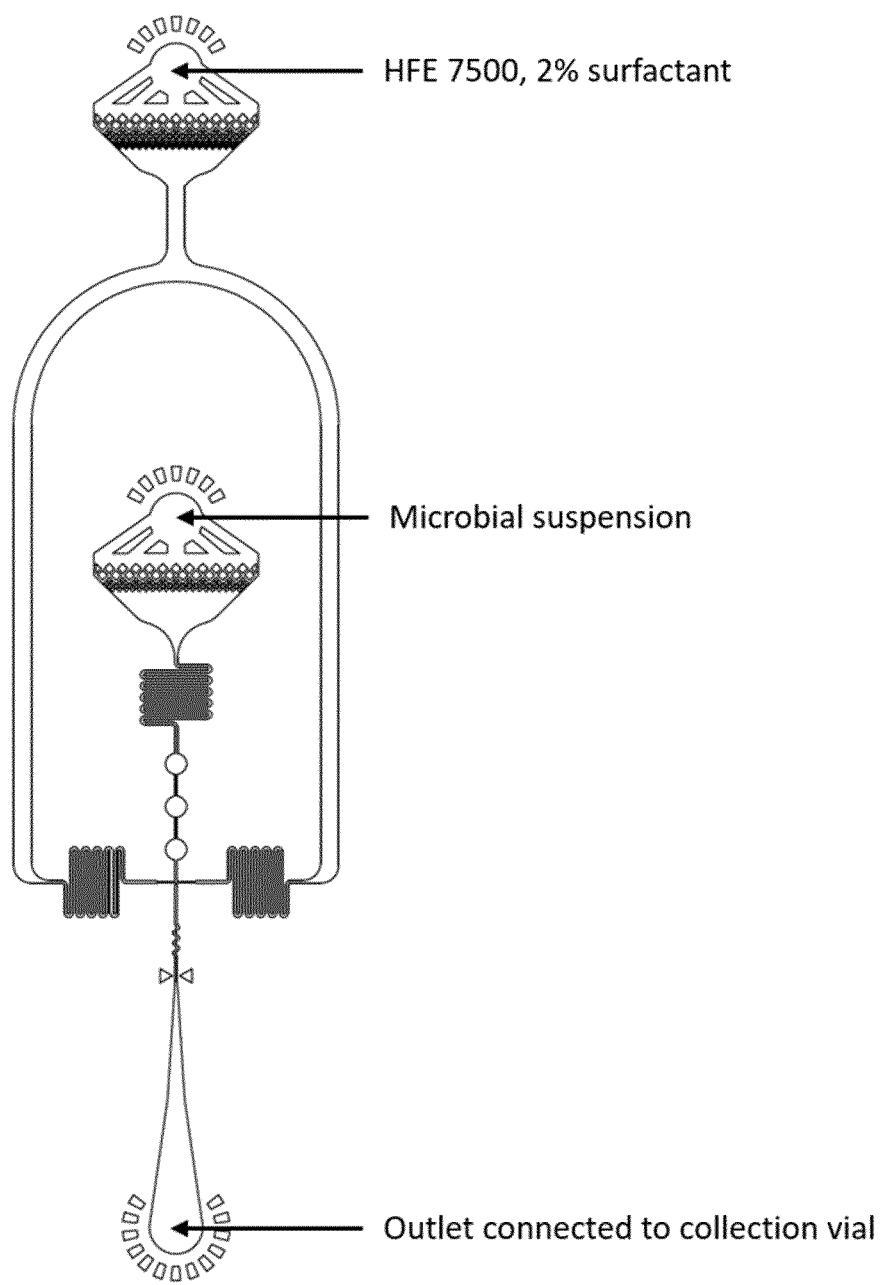
FIG. 8 shows a flow focusing device used to perform the method according to the invention disclosed herein.
Figure 9:
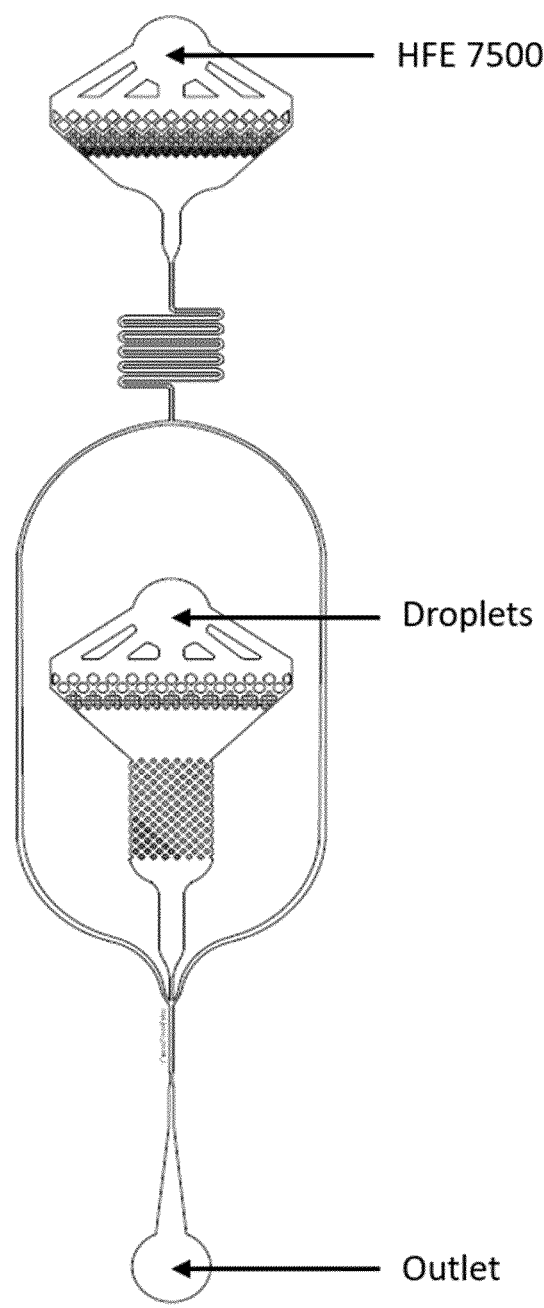
FIG. 9 shows a reinjection device used to perform the method according to the invention disclosed herein.
Figure 10:
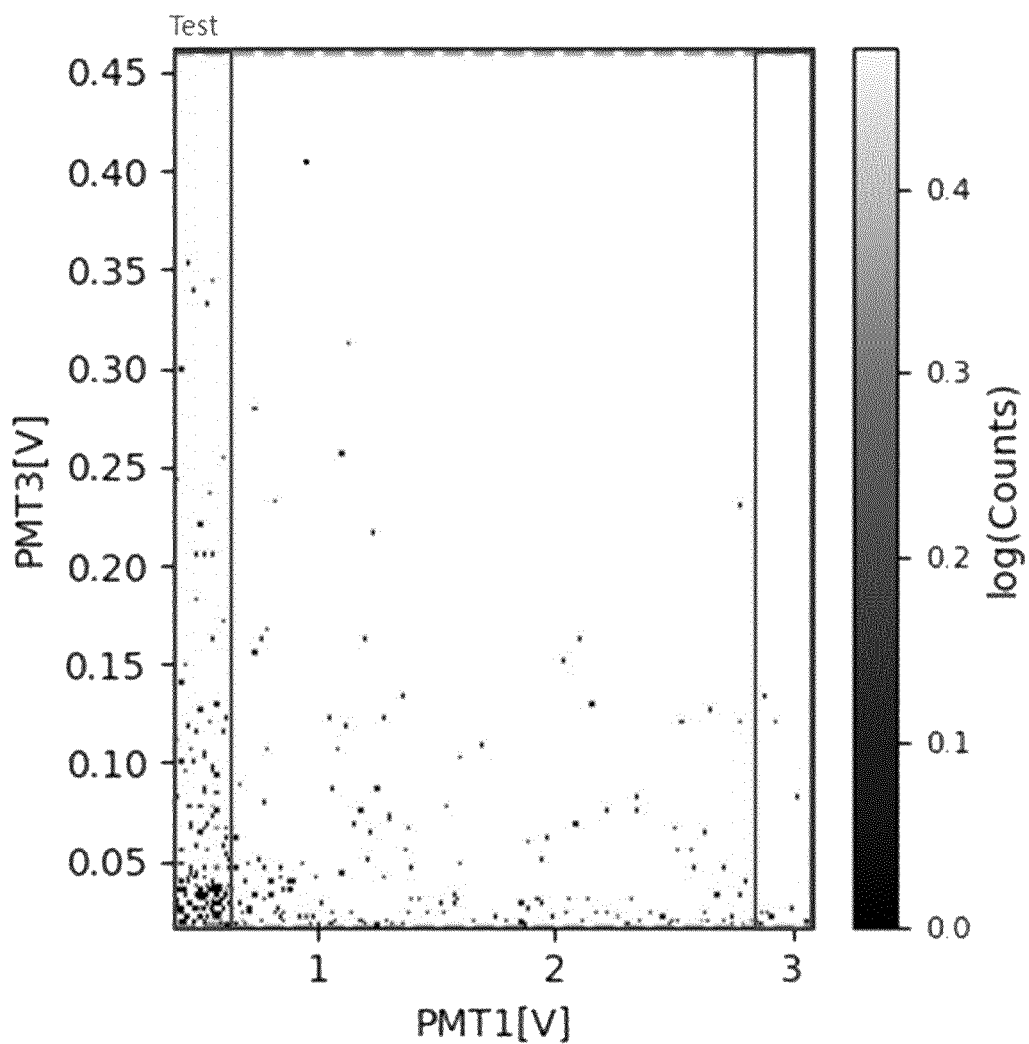
FIG. 10 shows a dot plot histogram of the results obtained by performing the method according to the invention disclosed herein.

The invention claimed is:
1. A method for the identification of a first microorganism potentially secreting an effector compound, said first microorganism thereby having either
  i) an inhibitory effect on the cell division activity of a second microorganism or
  ii) an enhancing effect on the cell division activity of a second microorganism, the method comprising:
    a) providing a cell from a first microorganism;
    b) incubating into a microdroplet the cell from the first microorganism which potentially produces an effector compound of interest;
    c) co-culturing the cell from the first microorganism obtained from step (b) and a cell from a second microorganism into a microdroplet;
    d) introducing the microdroplet of step c) into a microfluidic system; and
    e) analyzing in said microfluidic system the cell of the second microorganism for the exhibition of an enhanced growth effect or the exhibition of an inhibited growth effect stemming from said effector compound.

2. A method according to claim 1, additionally comprising the step of isolating the effector substance after step c.).

3. A method according to claim 1 or 2, wherein the first microorganism and/or second microorganism is a bacterial cell, fungal cell, yeast cell, algal cell, eukaryotic cell or a prokaryotic cell.

4. A method according to claim 1, wherein said first microorganism is from a natural sample suspected of comprising microorganisms that produce the desired effector substance or wherein the sample is from a variant strain pool generated by random mutagenesis.

5. A method according to claim 1, wherein the incubation is performed in the microfluidic system.

6. A method according to claim 1, wherein the effector compound is a primary metabolite selected from the group consisting of L- and D-amino acids; sugars and carbon sources selected from the group consisting of L-arabinose, N-acetyl-D-glucosamine, N-acetyl-D-mannosamine, N-acetylneuraminate, lactose, D-glucosamine, D-glucose-6-phosphate, D-xylose, D-galactose, glycerol, maltose, maltotriose, and melibiose; nucleosides selected from the group consisting of cytidine, guanine, adenine, thymidin, guanosine, adenosine; lipids selected from the group consisting of hexadecanoate and glycerol 3-phosphate; indole, maltohexose, maltopentose, putrescine, spermidine, ornithine, tetradecanoate, and nicotinamide adenine dinucleotide; or a secondary metabolite.

* * * * *